United States Patent [19]
Collins

[11] Patent Number: 5,782,873
[45] Date of Patent: Jul. 21, 1998

[54] METHOD AND APPARATUS FOR IMPROVING THE FUNCTION OF SENSORY CELLS

[75] Inventor: James J. Collins, Brighton, Mass.

[73] Assignee: Trustees of Boston University, Boston, Mass.

[21] Appl. No.: 703,674

[22] Filed: Aug. 27, 1996

Related U.S. Application Data

[60] Provisional application No. 60/005,343 Oct. 11, 1995.

[51] Int. Cl.⁶ .................................................. A61N 1/00
[52] U.S. Cl. .................................. 607/2; 607/46; 607/62
[58] Field of Search .............................. 607/46, 62, 2; 128/741, 744

[56] References Cited

U.S. PATENT DOCUMENTS

| | | |
|---|---|---|
| 4,503,863 | 3/1985 | Katims ........................... 607/62 |
| 4,632,116 | 12/1986 | Rosen et al. ................... 607/62 |
| 4,803,988 | 2/1989 | Thomson ........................ 607/70 |
| 4,813,399 | 3/1989 | Gordon . | 
| 4,881,526 | 11/1989 | Johnson et al. . |
| 5,005,574 | 4/1991 | Fearnot et al. . |
| 5,083,564 | 1/1992 | Scherlag ......................... 607/9 |
| 5,360,438 | 11/1994 | Fisher ........................... 607/53 |

FOREIGN PATENT DOCUMENTS

| | | |
|---|---|---|
| 0019444 | 11/1980 | European Pat. Off. . |
| 0460320 | 12/1991 | European Pat. Off. . |
| 3538662 | 5/1987 | Germany . |
| 4408110 | 9/1994 | Germany . |
| 9105523 | 5/1991 | WIPO . |
| 9301862 | 3/1993 | WIPO . |
| 9312835 | 7/1993 | WIPO . |
| 9415540 | 7/1994 | WIPO . |
| 9615632 | 2/1996 | WIPO . |

*Primary Examiner*—William E. Kamm
*Assistant Examiner*—George R. Evanisko
*Attorney, Agent, or Firm*—Samuels, Gauthier, Stevens & Reppert

[57] ABSTRACT

Method and system for enhancing the function of sensory cells are disclosed. The method comprises locating a sensory cell area associated with the sensory cell whose function is to be enhanced and inputting a bias signal to the sensory cell area. The apparatus comprises a signal processor for producing a bias signal and an input device for inputting the bias signal to a sensory cell area associated with a sensory cell whose function is to be enhanced. Inputting the bias signal to a sensory cell area effectively lowers the threshold of sensory cells with which the sensory cell area is associated.

39 Claims, 1 Drawing Sheet

METHOD AND APPARATUS FOR IMPROVING THE FUNCTION OF SENSORY CELLS

This application claims the benefit of U.S. Provisional Application No. 60/005,343, filed Oct. 11, 1995.

BACKGROUND

1. Field of the Invention The invention relates to improving the function of sensory cells. More specifically, this invention relates to a method and apparatus for effectively lowering the threshold of a sensory cell by inputting a noise signal to a sensory cell.

2. Background of the Invention

The nervous system can be divided into two main parts: the autonomic portion and the sensory portion. As used herein, the term autonomic refers to that portion of the nervous system that controls the functions of the body, such as, pumping blood, and perspiring, which occur involuntarily. The term sensory, on the other hand, refers to the systems of the nervous system which controls interaction of the body with its surroundings. Examples of sensory systems include the proprioceptive system, the auditory system, the visual system, the vibration-sensation system, the temperature-sensation system and the touch-pressure sensation system.

The sensory systems can be divided into two types of cells: sensory transducers and sensory neurons. Sensory transducers are cells such as the rod and cone cells in the visual system and the hair cells of the auditory system which interact with the surroundings. Sensory transducers convert an input signal, for example, a sound wave, into an electrical signal which the nervous system can process. Sensory neurons are cells which convey signals produced at the sensory transducers through the nervous system. Sensory transducers can actually be thought of as specialized neurons. Therefore, the term sensory cell will be used to describe both sensory neurons and sensory transducers.

A sensory cell typically includes a cell body or soma and one or more long processes: a single axon and dendrites. The single axon functions to carry signals from the soma while the dendrites carry signals to the soma. These processes act as cables conveying signals through the nervous system. Processes, however, are poorly insulated (which results in excessive leakage current) and are covered with a capacitive membrane (which gives rise to a propagation delay and signal decay over time). Therefore, processes are not good conductors and do not rely on passive transmission to conduct a signal. Rather, processes convey nerve impulses through an active electrochemical mechanism called an action potential.

When a process is at equilibrium, there is a potential difference maintained across the membrane of a process due to differing ion concentrations (for example $Na^+$, $K^+$, $Cl^-$ and $Ca^{2+}$) on either side of the membrane with the area within the membrane being at a lower potential than the area on the outside of the membrane. The ions chiefly responsible for conveying signals through processes are $Na^+$ and $K^+$. As is in most cells, a gradient is maintained in the concentration of these two ions by a $Na^+$—$K^+$ pump. The $Na^+$—$K^+$ pump maintains the concentration of $Na^+$ about 9 times lower inside the process than outside the process and the concentration of $K^+$ about 20 times higher inside the process than outside the process. The membrane, however, contains channels through which $Na^+$ and $K^+$ may pass. These channels are closed at equilibrium, but they open in response to a disturbance giving rise to a voltage. That is, they are voltage-gated.

An action potential is triggered (and a sensory cell "fires") when a disturbance of sufficient magnitude causes a localized depolarization of the membrane of a first magnitude sufficient to open the voltage-gated $Na^+$ channels. The opening of the voltage-gated $Na^+$ channels causes an influx of $Na^+$ which leads to depolarization in adjacent areas of the process. The further depolarization leads to voltage-gated $Na^+$ channels opening in the adjacent areas thereby causing the disturbance to propagate through the process. Equilibrium is restored, by, among other things, the opening of the voltage gated $K^+$ channels when the depolarization reaches a second magnitude. When the voltage gated $K^+$ channels open there is an outflux of $K^+$ ions leading to a decrease in the magnitude of depolarization thereby causing the voltage-gated $Na^+$ channels to close.

Sensory cells are typically threshold-based units. That is, if an initial disturbance to a cell is of insufficient magnitude, the resulting depolarization will be insufficient to open the voltage gated channels and will thus dissipate due to leakage current and the propagation delay caused by membrane capacitance. Such a disturbance is called a subthreshold signal.

Various diseases, disorders and injuries may increase the threshold of sensory cells. Such an increase in threshold may result in disturbances which are sufficient to cause a healthy sensory cell to "fire" being insufficient to cause the damaged sensory cell to fire. Thus, any damage the body sustains to any of the transducer cells of the sensory systems, for example, may lead to the consistent occurrence of subthreshold input signals. Also, genetic defects, for example, visual and auditory impairment, may lead to the consistent production of subthreshold input signals to sensory cells.

SUMMARY OF THE INVENTION

It is one object of the present invention to provide a method and system for enhancing the function of sensory cells.

It is another object of the present invention to enhance the ability of sensory cells to detect subthreshold input signals by adding noise to the input signal or by adding noise directly to the sensory cell. It is another object of the present invention to provide an analytical technique for determining when the signal-detection abilities of a sensory cell have been optimally enhanced.

In one embodiment, the present invention comprises a method for effectively lowering the threshold of a threshold-based sensory cell. In an initial step an area of the body associated with a sensory cell area is located. Once such an area has been located a bias signal is generated and input to the located area. The bias signal causes the threshold of sensory cells in the sensory cell area to be exceeded in response to a subthreshold input stimulus thereby effectively lowering the threshold of the sensory cells in the sensory cell area.

In another embodiment, the present invention comprises a system for effectively lowering the threshold of a sensory cell. The system comprises a transducer for transducing an input stimulus to a sensory cell area into an electrical signal, a signal processor for producing a bias signal in response to the electrical signal, and an input device for inputting the bias signal to an area of the body associated with the sensory cell area. The bias signal, coupled with the subthreshold input stimulus, causes the threshold of sensory cells associated with the sensory cell area to be exceeded thereby effectively lowering the threshold of the sensory cells. The system also comprises a controller for controlling the transducer, signal processor and input device to operate in response to a subthreshold input stimulus.

BRIEF DESCRIPTION OF THE DRAWINGS

The features and objects of the present invention, and the manner of attaining them is explained in detail in the following DETAILED DESCRIPTION OF THE PREFERRED EMBODIMENTS of the invention when taken in conjunction with the accompanying drawings wherein.

DETAILED DESCRIPTION OF THE PREFERRED EMBODIMENTS

The preferred embodiments of the present invention provide a method and system for enhancing the function of a sensory cell. The method comprises adding an externally produced signal to the input signal of a sensory cell, or to the sensory cell itself, so that the input signal is converted from a subthreshold input to a suprathreshold input. The externally produced signal biases the sensory cell thereby effectively lowering its threshold. The externally produced signal is, therefore, hereinafter referred to as a bias signal.

The method and system according to the preferred embodiments of the present invention are useful, for example, to enhance the function of sensory neurons in healthy individuals as well as in individuals with disorders, diseases and/or injuries. For example, the method and system could be applied to individuals with elevated sensory thresholds, such as, older adults and patients with peripheral neuropathies or strokes.

Figure 1:
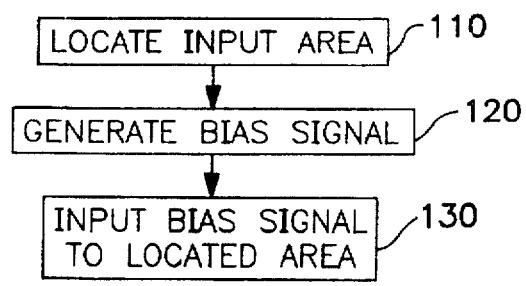
FIG. 1 is a flow chart of a method for enhancing the function of a sensory cell according to one embodiment of the present invention.

FIG. 1 is a flow chart of a method for enhancing the function of a sensory neuron according to one embodiment of the present invention. In step 110, an area associated with the sensory cell whose function is to be enhanced and to which a bias signal is to be input is located. The located area is hereinafter referred to as the input area. Once the input area has been located, the bias signal is generated in step 120. Then in step 130, the bias signal is input to the input area so as to effectively lower the threshold of sensory cells with which the input area is associated.

Figure 2:
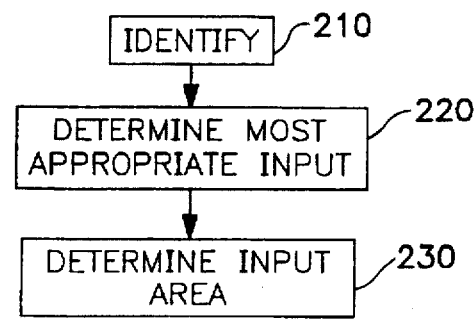
FIG. 2 is a flow chart of a method for locating an input area according to one embodiment of the present invention.

FIG. 2 is a flow chart showing one embodiment of locating an input area according to step 110. Locating the input area depends, inter alia, on the sensory system whose function is to be improved and the method by which a bias signal may be input to sensory cells associated with the sensory system. Step 210 is a preliminary step in which an identification scheme is undertaken to identify a particular sensory system whose function is to be enhanced. The identification scheme, to some extent, depends on the cooperation of the individual. That is, this step is similar to a diagnosis, however, the individual need not be suffering from any disease or disorder to be subject to the enhancement process contemplated herein. In one embodiment, the sensory system whose function is to be enhanced is one whose function has been degraded by disease. In an alternative embodiment, the sensory system to be enhanced is one which functions normally. In step 220, the most appropriate way of inputting a bias signal to the target sensory system is determined. The most appropriate input means depends on a number of factors including, the target sensory system, the nature of the transduction system for the target sensory system, the present state of the target sensory system (i.e., whether it is impaired or in any way dysfunctional), and the nature of the signal which is to be determined (e.g., the amplitude and frequency content of the signal). Input means which are appropriate in certain circumstances include, but are by no means limited to, nerve cuffs, implanted electrodes, surface electrodes, muscle stimulators, tendon stimulators and magnetic field stimulators. Once the most appropriate input means is determined in step 220, the input area is determined in step 230. The location of an input area depends on the same factors as the determination of the most appropriate input means. The location of the input area, however, varies for a particular input means depending on, among other factors, whether the target sensory system, is in any way dysfunctional, the cause and location of any such dysfunctionality, and the nature of the stimulator to be used. More specifically, if a dysfunctionality caused by some physical damage to sensory cells is present in the sensory system, it may be necessary to locate the input area such that the bias signal will bypass the physical damage causing the dysfunctionality. Further, the fact that some stimulators, e.g. implanted electrodes, may require invasive procedures while others, e.g., surface electrodes, require only non-invasive procedures is also a factor to consider.

Figure 3:
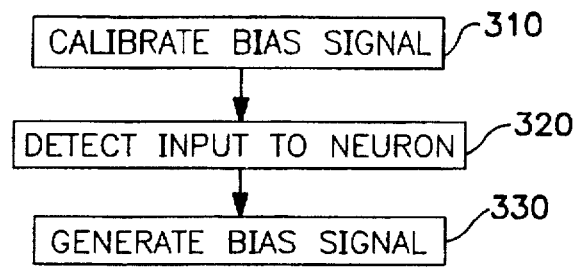
FIG. 3 is a flow chart of a method for generating a bias signal according to one embodiment of the present invention.

Once the input area is determined and the input means installed, the bias signal to be input is generated. FIG. 3, shows one embodiment of a method of generating a bias signal. In an initial step 310, the bias signal is calibrated. That is, an optimal level for the bias signal is determined. Depending on the determinations of steps 220 and 230, there exists a particular form of bias signal for which the signal-detection ability of a given neuron in the target sensory system is optimally enhanced. For example, a bias signal having parameters with certain predetermined values will give rise to optimal enhancement. Calibration helps to ensure that certain parameters of the bias signals generated will be adjusted to achieve optimal enhancement. Examples of signal parameters of the bias signal which may be calibrated are amplitude, frequency, offset (D.C. bias), intensity, variance, frequency bandwidth and spectral characteristics in general. Calibration is typically accomplished prior to installation of the enhancement system and may be accomplished intermittently while the enhancement system is installed. If calibration is to take place while the enhancement system is installed, then it is desirable to install the enhancement system so it is accessible from the outside of the body so that calibration may be accomplished non-invasively.

In one embodiment, the calibration is accomplished by inputting an input signal of interest to a sensory cell coupled with a bias signal produced by the enhancement system. The response of the sensory cell to the combined input is recorded as a function of a parameter of interest in the bias signal. That is, the response of the sensory cell is recorded as a parameter of interest in the bias signal is modulated. Using the recorded results, the coherence between the combined input and the response of the sensory cell is then characterized by computing some measure such as the cross-correlation coefficient described below. The response of the sensory cell is maximally enhanced when the coherence measure is maximized. This maximally enhanced response corresponds to some value or range of values of the bias signal parameter of interest which can be determined by, for example, examining a record of the bias signal. Thus, an optimal value or range of values for the parameter of interest of the bias signal is determined. The process can be repeated using other input signals and parameters of interest thereby determining a bias signal with optimal parameters for input signals with varying parameters.

According to one embodiment of the present invention, the bias signal is optimized by examining the cross-correlation coefficient, $C_1$:

$$C_1 = \frac{C_0}{[S^2(t)]^{\frac{1}{2}} [\overline{(R(t) - \overline{R(t)})^2}]^{\frac{1}{2}}}$$

where $$C_0 = \overline{S(t)R(t)}$$

where S(t) is the input signal, R(t) is the output of the sensory neuron or sensory system (e.g., the neural mean firing rate signal or the neural spike train), and the overbar denotes an average over time. S(t) and R(t) can be measured with any appropriate transducers, for example, a needle electrode may be used to measure the output of a neuron. Maximizing $C_1$ corresponds to maximizing the coherence between the input signal S(t) and the neuron's output R(t). The value of $C_1$ for a given input signal will depend upon the parameter of interest of the bias signal. Thus, a bias signal having parameters which will produce the desired output R(t) may be determined.

The results of the calibration process may be utilized, for example, by modulating the bias signal in response to an input signal or by determining a set of parameter values which, on average, will achieve optimal enhancement for any input signal. In the first instance, parameter values for the bias signal are, for example, tabulated against parameters of the input signal. Upon occurrence of an input signal, certain parameters of the input signal are measured and a bias signal having corresponding parameter values is generated by referencing the tabulated results. In this way, the bias signal is modulated or optimized for each particular input signal. In the second instance, a single set of parameter values which will achieve optimal enhancement for most signals is calculated and used to generate a bias signal which is for use in response to every input.

After the input device has been calibrated and installed, in one embodiment, an input signal to the neuron is detected. As will be explained in conjunction with FIG. 4, one embodiment of a system for enhancing the function of a sensory neuron includes signal detection capabilities, for example, a transducer and signal processor. Thus, in step 320, input signals to the neuron are detected using the signal detection capabilities.

Once an input signal is detected in step 320, a bias signal is generated in step 330. As explained above with respect to the calibration process, the bias signal has either parameters which are modulated depending on certain parameters of each input signal or a constant, nonmodulated, set of parameters which are designed to optimally enhance the function of a sensory cell in response to most input signals. If a bias signal having a non-modulated set of parameters is used, then a somewhat simpler input system is used. In general, the nature of the bias signal to be used, that is, modulated or non-modulated, depends on the nature of the sensory system to be enhanced. Once the bias signal is generated, it is input to the neuron in step 130.

In the embodiments described above, a bias signal is produced only in response to the detection of an input signal to the neuron. In an alternative embodiment, after the input device has been calibrated and installed, a bias signal is continuously generated and input to the neuron. That is, an input signal does not need to be detected. In a method according to this embodiment, the bias signal is either modulated or non-modulated. If the bias signal is modulated, then the continuously generated bias signal is modulated as described above, when an input signal is detected. If a non-modulated bias signal is used in this embodiment, then a simplified input system may be used. As discussed above, whether a modulated or non-modulated bias signal is used depends upon, inter alia, the nature of the system to be enhanced.

In another embodiment, a distributed enhancement process is used. In this embodiment, the enhancement process described above is modified such that a bias signal is generated and input to neurons at a plurality of locations to stimulate an array of sensory cells and thereby provide a distributed enhancement effect. In this distributed enhancement system, as above, either a continuous or non-continuous, and modulated or non-modulated bias signals may be used. As one example, if the sensory function of the urinary tract is to be enhanced, a bias signal may be input to a number of distributed points around the bladder so that improved fullness sensation is obtained.

Figure 4:
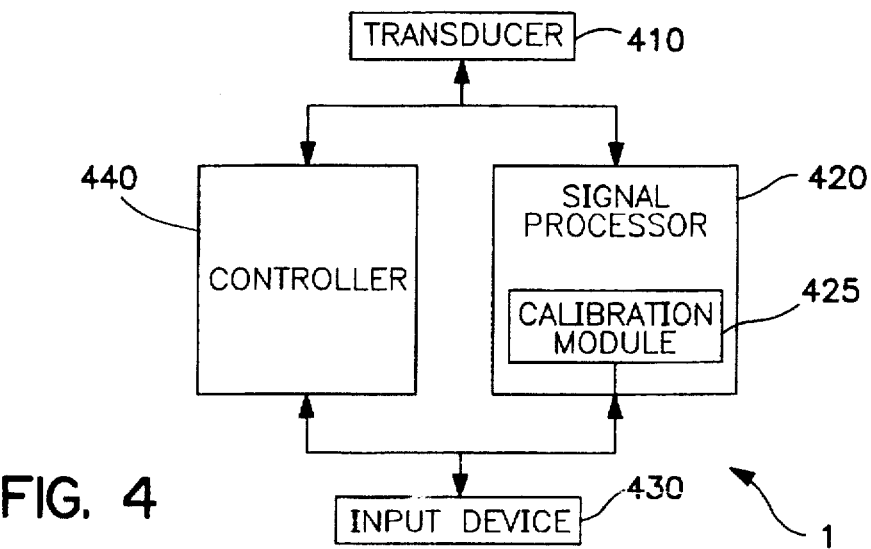
FIG. 4 is a schematic depiction of a system for enhancing the function of a sensory cell according to one embodiment of the present invention.

One embodiment of an enhancement system 1 for implementing the method for enhancing the function of a sensory neuron is shown in FIG. 4. Enhancement system 1 comprises a transducer 410, a signal processor 420, an input device 430 and a controller 440. Enhancement system 1 operates on electrical signals. An input signal to a sensory cell is typically initiated by contact with the outside world which contact is generally not in the form of an electrical signal. An input signal might be initiated by, for example, a touch, a movement of a body segment, a sound wave or light. One function of transducer 410 is to detect input signal initiating contacts and convey the contact to enhancement system 1 generally and signal processor 420 specifically. Another function of transducer 410 is to convert an input signal initiating contact into a signal in a form which is usable by enhancement system 1. The mechanism used for transducer 410 depends on the sensory system targeted. As an example, if the auditory system is being targeted for enhancement, transducer 410 may take the form of a stimulating electrode or an array of stimulating electrodes arranged in the vicinity of the ear. As another example, if the proprioceptive system is being targeted for enhancement, transducer 410 is a tendon stimulator, implemented by way of a piezoelectric transducer, installed or attached via elastic straps to a tendon or parent muscle associated with the sensory cells whose function is to be enhanced. As still another example, if the vibration or touch-pressure sensation system is being targeted for enhancement, transducer 410 is a surface electrode installed or applied over the skin of the area of the body containing the cells to be stimulated. Such an electrode is attached using flexible electrode/skin interfaces.

Signal processor 420 produces a bias signal to be input to the sensory system targeted for enhancement through input device 430. Signal processor 420 is electrically connected to transducer 410, input device 430 and controller 440. As discussed above, a bias signal may be either continuous or non-continuous and modulated or non-modulated. The form of signal processor 420 depends upon the desired form of the bias signal to be produced. In one embodiment, where a non-continuous, modulated bias signal is desired, signal processor 420 preferably includes both signal detection capabilities and look-up table capabilities to store parameter values for the bias signal. In another embodiment, where a constant, non-modulated bias signal is desired, signal processor 420 does not necessarily require signal detection capabilities and look-up table capabilities. In one embodiment, signal processor 420 is either a special function IC or a general micro-processor and is preferably small, lightweight and portable. Further, signal processor 420 preferably includes signal conditioning and data acquisition abilities. In one embodiment, a PCM CIA chip or card is used as signal processor 420.

Signal processor 420 also includes calibration module 425. Calibration module 425 enables adjustment of the bias signal produced by signal processor 420. For example, for optimal enhancement, signal processor 420 produces a bias signal having predetermined parameters (for example, a predetermined amplitude and frequency) in response to a particular signal received from transducer 410. If these predetermined parameters of bias signal are not properly adjusted, the bias signal will not optimally enhance the function of the targeted sensory system. Calibration module 425 enables these predetermined parameters to be adjusted so that an optimal bias signal is produced. Calibration is typically accomplished prior to installation of enhancement system 1 and may be accomplished intermittently while enhancement system 1 is installed. If calibration is to take place while enhancement system 1 is installed, then it is desirable to install signal processor 420 so it is accessible from the outside of the body so that calibration may be accomplished non-invasively. In an alternative embodiment, signal processor 420 is provided with remote access capability enabling calibration to take place non-invasively whether or not signal processor is accessible from outside of the body.

Input device 430 conveys the bias signal produced by signal processor 420 to the targeted sensory system. Depending on what the targeted sensory system is, input device 430 might take a number of different forms as discussed above. Input devices which are appropriate in certain circumstances include, nerve cuffs, implanted electrodes, surface electrodes, muscle stimulators, tendon stimulators, and magnetic field stimulators. The manner in which input device 430 conveys the bias signal to the targeted sensory system depends on the form of input device 430 and the targeted sensory system. For example, a nerve cuff or implanted electrode is suitable for use when the urinary tract is the targeted sensory system and is typically implanted surgically and conveys the bias signal to the sensory components of the system. A muscle or tendon stimulator, on the other hand, is more suited to mechanically stimulate the proprioceptive system. Such a stimulator mechanically stimulates the proprioceptive system by vibrating a muscle or tendon associated with that system, for example a muscle in the vicinity of a joint. Muscle or tendon stimulators can be applied non-invasivly using, for example, an elastic band. In one embodiment, where the targeted sensory system is the vibration or touch-pressure sensation system, a surface electrode-based system is used as input device 430. Specifically, the Glove Electrode, the Sock Electrode and the Sleeve Electrode, sold under the name Electro-Mesh™ may be used as input device 430. The surface electrode system is placed over the body part of interest, eg., the hand or foot. Still further, input device 430 may be a magnetic field stimulator used either non-invasively or invasivly. For example, a magnetic field stimulator may be used to stimulate cutaneous sensory neurons by positioning the stimulator on the exterior of the body in the vicinity of the sensory cells to be stimulated using elastic bands. A magnetic field stimulator may be used invasively, for example, by surgically implanting the stimulator to stimulate sensory neurons in the area of the bladder.

Controller 440 controls interaction between transducer 410, signal processor 420 and input device 430. The implementation for controller 440 depends upon, among other things, the form of bias signal desired. That is, where a non-continuous, modulated bias signal is desired, controller 440 may be implemented using a microprocessor. In a simpler embodiment, where a continuous, non-modulated bias signal is desired, controller 440 may be implemented using a switch which simply activates the enhancement signal. Alternatively, signal processor 420 may be adequate, so that controller 440 is unnecessary for such an embodiment. By way of example only, controller 440 comprises a microprocessor with suitable programming, or any digital controller. In one embodiment, controller 440 is implemented with the aforementioned PCM CIA chip or card.

Although the present invention has been described in detail, it should be understood that various changes, substitutions, and alterations can be made without departing from the intended scope as defined by the appended claims.

I claim:

1. A method for enhancing the ability of a threshold-based sensory cell to respond to a subthreshold stimulus comprising the steps of:
   a) locating an area of the body associated with a sensory cell area;
   b) generating a bias signal; and,
   c) inputting the bias signal to the located area wherein the bias signal causes the threshold of sensory cells in the sensory cell area to be exceeded in response to the subthreshold stimulus thereby effectively lowering the threshold of the sensory cells in the sensory cell area, wherein the step of generating a bias signal further comprises the step of transducing the subthreshold stimulus to the sensory cell area into an electrical signal and generating the bias signal in response to the electrical signal.

2. The method of claim 1 wherein the located area comprises a nerve.

3. The method of claim 1 wherein the located area comprises the sensory cell area.

4. The method of claim 1 wherein the located area comprises a muscle.

5. The method of claim 1 wherein the bias signal comprises a noise signal.

6. The method of claim 1 further comprising:
   sensing said subthreshold stimulus;
   wherein the bias signal comprises an electrical signal which is modulated in response to the sensed subthreshold stimulus.

7. The method of claim 1 wherein the bias signal comprises a periodic signal.

8. The method of claim 1 wherein the bias signal comprises a high frequency deterministic signal.

9. The method of claim 1 wherein the bias signal comprises a magnetic field.

10. The method of claim 9 wherein the magnetic field comprises a randomly fluctuating field intensity.

11. The method of claim 1 wherein the bias signal comprises a mechanical stimulus.

12. The method of claim 1 wherein the bias signal comprises a predetermined signal.

13. The method of claim 12 wherein the predetermined signal is calibrated according to a function which the threshold-based sensory cell performs.

14. A method for enhancing the ability of a threshold-based sensory cell to respond to a subthreshold stimulus comprising the steps of:

a) sensing the subthreshold stimulus to a sensory cell area;

b) generating an electrical signal in response to the subthreshold stimulus; and c) inputting the electrical signal to the sensory cell area wherein the electrical signal causes the threshold of sensory cells in the sensory cell area to be exceeded thereby effectively lowering the threshold of the sensory cells in the sensory cell area.

15. The method of claim 14 further comprising the step of:

d) determining an optimal level for a parameter of the electrical signal, wherein the step of inputting an electrical signal comprises inputting an electrical signal having the parameter with the optimal level.

16. The method of claim 15 wherein the parameter comprises frequency.

17. The method of claim 15 wherein the parameter comprises amplitude.

18. The method of claim 14 wherein the step of generating comprises generating a noise signal in response to the sensed subthreshold stimulus.

19. The method of claim 14 wherein the step of generating comprises generating the electrical signal in response to the subthreshold stimulus, and modulating the electrical signal in response to the sensed subthreshold stimulus.

20. The method of claim 14 wherein the step of inputting comprises locating a sensory nerve associated with the sensory cell area, implanting a nerve cuff around the located sensory nerve and inputting the electrical signal through the implanted nerve cuff.

21. The method of claim 14 wherein the step of inputting comprises locating a sensory nerve associated with the sensory cell area, positioning a surface electrode on the exterior of the body in an area associated with the sensory cell area and inputting the electrical signal through the surface electrode.

22. The method of claim 14 wherein the step of inputting comprises locating the sensory cell area, implanting electrodes at the sensory cell area and inputting the electrical signal through the implanted electrodes.

23. The method of claim 14 wherein the step of inputting comprises positioning a muscle stimulator in an area around a muscle associated with the sensory cell area and inputting the electrical signal through the muscle stimulator, wherein the muscle stimulator stimulates a muscle thereby stimulating the sensory cell with which the muscle is associated.

24. The method of claim 23 wherein the muscle stimulator mechanically stimulates the muscle.

25. The method of claim 14 wherein the step of inputting comprises positioning a tendon stimulator in an area around a tendon associated with the sensory cell area and inputting the electrical signal through the tendon stimulator, wherein the tendon stimulator stimulates a tendon thereby stimulating the sensory cell with which the tendon is associated.

26. The method of claim 25 wherein the tendon stimulator mechanically stimulates the tendon.

27. The method of claim 14 wherein the sensory cell area comprises at least one sensory neuron.

28. The method of claim 14 wherein the sensory cell area comprises at least one sensory receptor.

29. The method of claim 14 wherein the sensory cell area is associated with the proprioceptive system.

30. The method of claim 14 wherein the sensory cell area is associated with the urinary tract.

31. The method of claim 30 wherein the sensory cell area is associated with the bladder.

32. The method of claim 14 wherein the sensory cell area is associated with the circulatory system.

33. The method of claim 32 wherein the sensory cell area is associated with the heart muscle.

34. The method of claim 14 wherein the sensory cell area is associated with the respiratory system.

35. The method of claim 14 wherein the sensory cell area is associated with the auditory system.

36. The method of claim 14 wherein the sensory cell area is associated with the visual system.

37. The method of claim 14 wherein the sensory cell area is associated with the vibration-sensation system.

38. The method of claim 14 wherein the sensory cell area is associated with the temperature-sensation system.

39. The method of claim 14 wherein the sensory cell area is associated with the touch-pressure sensation system.

* * * * *